United States Patent [19]

Shaw

[11] Patent Number: 5,457,234
[45] Date of Patent: Oct. 10, 1995

[54] PROCESS FOR TREATING ORGANIC POLYSULFIDE COMPOUNDS

[75] Inventor: James E. Shaw, Bartlesville, Okla.

[73] Assignee: Phillips Petroleum Company, Bartlesville, Okla.

[21] Appl. No.: 262,712

[22] Filed: Jun. 20, 1994

[51] Int. Cl.$^6$ .............................. C07C 319/22
[52] U.S. Cl. ............................................ 568/21
[58] Field of Search .................................. 568/21

[56] References Cited

U.S. PATENT DOCUMENTS

| | | | |
|---|---|---|---|
| 3,075,019 | 1/1963 | Webb et al. | 568/21 |
| 4,827,040 | 5/1989 | Labat et al. | 568/21 |
| 4,876,389 | 10/1989 | Gongora et al. | 568/26 |
| 4,933,481 | 6/1990 | Vallee et al. | 568/26 |
| 5,174,922 | 12/1992 | Perozzi et al. | 252/395 |
| 5,206,439 | 4/1993 | Shaw | 568/21 |
| 5,218,147 | 6/1993 | Shaw | 568/21 |
| 5,312,992 | 5/1994 | Clark et al. | 568/21 |

FOREIGN PATENT DOCUMENTS

| | | | |
|---|---|---|---|
| 0076376A1 | 4/1983 | European Pat. Off. | C07C 149/12 |
| 554011 | 8/1993 | European Pat. Off. | 568/21 |
| 55-47649 | 4/1980 | Japan | 568/21 |
| 58-140063 | 8/1983 | Japan | C07C 149/12 |
| 62-145057 | 6/1987 | Japan | 568/21 |

*Primary Examiner*—James H. Reamer
*Attorney, Agent, or Firm*—Lucas K. Shay

[57] ABSTRACT

A process for reducing the metal corrosiveness of an organic polysulfide comprises contacting the polysulfide with a metal such as a transition metal at an elevated temperature. A process for reducing the concentration of a polysulfide, having four or more sulfur atoms in the polysulfide molecule, in a polysulfide mixture is also provided which comprises contacting the polysulfide mixture with a metal such as a transition metal. Further provided is a process for reducing the concentration of an organic trisulfide in a mixture of an organic disulfide and trisulfide wherein the process comprises contacting the mixture with a metal such as a transitional metal.

31 Claims, No Drawings

PROCESS FOR TREATING ORGANIC POLYSULFIDE COMPOUNDS

FIELD OF THE INVENTION

The present invention relates to a process for treating organic polysulfide compounds and to a product thereby.

BACKGROUND OF THE INVENTION

Organic polysulfides containing two to five or even more sulfur atoms in the molecules have been found useful for many purposes such as additives for elastomers, antioxidants for lubricating oils, intermediates for the production of organic chemicals, insecticides, germicides and as an additive to diesel fuels to improve the octane number and ignition qualities of these fuels. These compounds have also been found useful in the compounding of extreme pressure lubricants and in the acceleration of rubber treating processes.

Such polysulfide compounds can be prepared by reacting mercaptans with elemental sulfur in the presence of a basic catalyst. For example, Biensan et al (U.S. Pat. No. 3,308, 166) discloses that polysulfides can be prepared from a mercaptan and sulfur catalyzed by an amine using an alcohol promoter.

However, it has been shown that the polysulfide compounds cause metal corrosion partly due to the presence of polysulfide compounds having four or more sulfur atoms. A small quantity of these polysulfide compounds having four or more sulfur atoms are always present when a polysulfide compound having less than four sulfur atoms is prepared. Therefore, there is need to reduce the metal corrosiveness of the polysulfide compounds. It would also be a significant contribution to the art if a process were developed for reducing the metal corrosiveness of organic polysulfide compounds.

SUMMARY OF THE INVENTION

An object of the present invention is to provide a process for treating organic polysulfide compounds. Another object of the invention is to reduce the metal corrosiveness of organic polysulfide compounds. A further object of the present invention is to reduce the concentration of polysulfide compounds having four or more sulfur atoms in the molecules in organic polysulfide compound preparations which are mainly trisulfides. Still another object of the invention is to reduce the concentration of an organic trisulfide compound from a mixture containing an organic disulfide and an organic trisulfide. Other objects and advantages will become more apparent as the invention is more fully disclosed hereinbelow.

According to a first embodiment of the present invention, a process which can be used to treat organic polysulfide compounds is provided. The process comprises contacting an organic polysulfide with a metal under conditions sufficient to reduce the metal corrosiveness of the polysulfide wherein the polysulfide and the metal are each present in an amount effective to substantially reduce the metal corrosiveness of the polysulfide.

According to a second embodiment of the present invention, a process for reducing the concentration of polysulfide compounds having four or more sulfur atoms in the molecules in a mixture of organic polysulfides is provided which comprises contacting a mixture of organic polysulfides with a metal under conditions sufficient to reduce the concentration of the polysulfide compounds having four or more sulfur atoms in the mixture wherein the metal and the mixture of organic polysulfides are each present in a sufficient amount to effect the reduction.

According to a third embodiment of the present invention, a process for reducing the concentration of an organic trisulfide in a mixture of organic disulfides and trisulfides is provided which comprises contacting a mixture of organic disulfides and trisulfides with a metal under conditions sufficient to reduce the concentration of the organic trisulfide wherein the metal and the mixture of organic disulfides and trisulfide are each present in a sufficient amount to effect the reduction.

DETAILED DESCRIPTION OF THE INVENTION

According to the first embodiment of the present invention, any organic polysulfide compounds having the formula of $R-S_n-R$, wherein each R can be the same or different and is each a hydrocarby radical having 1 to about 30, preferably about 1 to about 20, and most preferably 2 to 15 carbon atoms and n is a number from 2 to about 10, preferably 2 to 8, can be treated by the process of the present invention. The hydrocarbyl radical can be linear or branched and can be alkyl, aryl, cycloalkyl, alkaryl, aralkyl, alkenyl radicals, or combinations of two or more thereof. Preferably the hydrocarbyl radical is an alkyl radical.

The polysulfide can be prepared by any process known in the art such as, for example, the process disclosed in U.S. Pat. No. 5,218,147, disclosure of which is incorporated herein by reference.

"The polysulfide can be prepared by the reaction of mercaptans and elemental sulfur catalyzed by a basic catalyst. The reaction is depicted as $RSH+RSH+(n-1)S \rightarrow RS_nR+H_2S$ where R and n are the same as those described above. The reaction can be carded out under any reaction condition, in any suitable reaction vessel. The basic catalyst can be a metal hydroxide such as sodium hydroxide, a metal oxide or a metal salt such as MgO and $NaCO_3$, and an amine such as triethylamine. Generally, one of the reactants, either the mercaptan or sulfur, is slowly added to the other reactant in the presence of a basic catalyst. The amount of sulfur added depends on the desired sulfur content of the polysulfide product. For an average sulfur content of n sulfurs per polysulfide molecule, (n-1) moles of sulfur must be added and 1 mole of hydrogen sulfide will be released per 2 moles of mercaptans reacted. The weight of the basic catalyst as a percentage of the weight of mercaptan should be 0.05 to 5%, preferably 0.1 to 2.0%, and most preferably 0.2 to 1.0%".

Any metal, preferably a transition metal that forms a metal sulfide, can be used in the present invention. Examples of suitable metals include, but are not limited to, zinc, copper, nickel, silver, or combinations of two or more thereof. The presently preferred metal is copper for it is readily available. Any physical forms of the metal such as powder, granule, dust, shot, turnings, and combinations can be employed. The preferred physical form is powder, or dust, or combination thereof because these forms have more surface area for contacting and they are easy to handle.

According to the present invention, any weight ratio of the metal to the polysulfide can be used so long as the ratio is effective to reduce the metal corrosiveness of the polysulfide as compared to the polysulfide which is not subject to the process of the present invention. For example, the weight ratio can be in the range of from about 0.001:1 to about 10:1, preferably about 0.005:1 to about 1:1, and most preferably 0.01:1 to 0.5:1.

According to the present invention, the contacting of the polysulfides and the metal is carried out under conditions that are effective to reduce the metal corrosiveness of the polysulfide as compared to the polysulfide which is not subject to the process of the present invention. Generally, the conditions can include a temperature in the range of from about 20° C. to about 300° C., preferably about 50° C. to about 250° C., and most preferably 80° C. to 200° C.; a pressure in the range of from about 0 to about 500 psig, preferably about 0 to about 200 psig, and most preferably 0 to 100 psig; and a time period from about 1 minute to about 10 hours, preferably about 5 minutes to about 3 hours, and most preferably 10 minutes to 2 hours.

The process of the first embodiment of the present invention can also be carried out in the presence of a solvent which is substantially miscible with the polysulfide and the metal. The presently preferred solvent is a hydrocarbon having up to about 20 carbon atoms. Examples of suitable solvents include, but are not limited to, water, methanol, ethanol, isopropanol, acetone, tetrahydrofuran, toluene, xylenes, decane, cyclohexane, or mixtures of two or more thereof. The weight ratio of the solvent, if employed, to the polysulfide can be in a wide range so long as the ratio is effective to facilitate the reduction of the metal corrosiveness of the polysulfide. For example, the ratio can be in the range of from about 0.01:1 to about 20:1, preferably 0.1:1 to 10:1.

The product polysulfide of the present invention can be recovered, if necessary, by any recovery method known to those skilled in the art. Examples of suitable methods include distillation, filtration, centrifugation, decantation, evaporation of solvent, sparging with an inert gas to remove solvent, and combinations of two or more thereof.

The second embodiment of the present invention is directed to the reduction of the concentration of organic polysulfide compounds, having four or more sulfur atoms in the molecules, in a mixture of polysulfide compounds. The mixture of polysulfide compounds generally contain a substantial concentration of an organic trisulfide, or organic disulfide, or mixtures thereof. The mixture of polysulfide compounds is contacted with a metal for the reduction of the polysulfides having four or more sulfur atoms in the molecules. The scope and the quantity of the polysulfides and the metal are the same as those described for the polysulfide and the metal in the first embodiment of the invention. The process of the second embodiment of the invention can be carried out under the same conditions as those disclosed in the first embodiment of the invention.

The third embodiment of the present invention is directed to the reduction of the concentration of an organic trisulfide compound in a mixture containing an organic disulfide and trisulfide. Generally, the disulfide is present in the mixture in substantially higher concentration than the trisulfide. The scope and quantities of the disulfide and trisulfide are the same as those disclosed in the first embodiment of the invention except that the n in the formula R—$S_n$—R is a number of 2 or 3. The scope and quantities of the metal is the same as that disclosed for the metal in the first embodiment of the invention. The process of the third embodiment of the invention can also be carried out under the same conditions recited for in the process of the first embodiment.

According to the present invention, the processes of all three embodiments of the invention disclosed above can be carried out either continuously or in batch mode using a suitable reaction vessel or device. For example, these processes can be carried out continuously employing a continuous stir tank or plug flow reactor whereby an organic polysulfide can be fed, contemporaneously with the feeding of a metal, to the reactor which is controlled under conditions disclosed above and the feed rates are adjusted such that an effective retention time is achieved to reduce the metal corrosiveness of the polysulfide. These processes can also be carried out by feeding a polysulfide compound or mixture of polysulfide compounds to a column packed with a suitable metal under conditions disclosed above followed by regeneration of the metal. The metal can be regenerated from its sulfide form by any method known to one skilled in the art such as, for example, treatment with a diluted acid. Because the choice of a suitable operation mode, or a suitable reaction vessel or device, or the metal regeneration method is a matter of preference to one skilled in the art, the description of which is omitted herein for the interest of brevity.

The following examples are provided to assist the understanding of the present invention and are not intended to unduly limit the scope of the present invention. The percentage shown in these examples is weight %. Gas chromatography (GC) analyses were carried out by injecting a sample (injection port temperature 200° C.) into a 20 inch by ⅛ inch column packed with 2% OV-101. The initial oven temperature was 50° C. and increased by 15° C. per minute to a final temperature of 250° C.

EXAMPLE I

This example illustrates the preparation of di-t-butyl trisulfide. To a 500 ml, 3-necked flask equipped with a thermowell, magnetic stir bar, pressure equalizing addition funnel, and condenser with line to flare was added 0.10 g 50% aqueous NaOH, 1.30 g Tergitol® 15-S-7 (an ethoxylated alcohol obtained from Union Carbide Corp.) and 39.2 g elemental sulfur. By means of the addition funnel, t-butyl mercaptan was added in portions until enough liquid was in the flask to stir and heat to 45° C. The remainder of the t-butyl mercaptan was added slowly at 45° C. Hydrogen sulfide was produced. The total mercaptan added was 135.3 g. The reaction mixture was then heated at 60° C. for 0.5 hour and then at 80° C. for 2.5 hours. By means of a gas dispersion tube, the reaction mixture was slowly sparged with $N_2$ at 80° C. for 2 hours.

The reaction mixture was cooled to 72° C. and the condenser was replaced with a Dewar (dry ice) condenser with a $N_2$ inlet at the top. Over 15 min, 5.0 ml propylene oxide was added. The reaction mixture was stirred at 72° C. for 2.25 hours and then slowly sparged with $N_2$ at 72° C. for 1.4 hours. The reaction mixture was filtered to give 134.4 g of a clear yellow liquid which contained (by GC) 86.0% di-t-butyl trisulfide, 5.1% disulfide, and 8.8% tetrasulfide.

EXAMPLE II

This example illustrates the removal of tetrasulfide from di-t-butyl trisulfide. To a 100 ml flask with thermowell, magnetic stir bar, and condenser was added 10.0 g of copper powder (Fisher Scientific C431) and 20.0 g of di-t-butyl trisulfide prepared in Example I. The mixture was heated to 150° C. with stirring and maintained at 150° C. for 30 minutes. After cooling, the reaction mixture was filtered to give 19 g (98% yield) of a clear yellow liquid which contained (by GC) 81.0% di-t-butyl trisulfide, 18.7% disulfide, and no tetrasulfide.

Another run was carried out the same way as described above except that the copper was reduced to 2.0 g. After 0.5 hour at 150° C., the reaction mixture contained 80.2% di-t-butyl trisulfide, 15.0% disulfide, and 3.4% tetrasulfide. No further reduction in tetrasulfide occurred after an additional 0.5 hour at 150° C., so another 2.0 g of copper powder was added. After 0.5 hour, the reaction mixture contained 74.3% trisulfide, 24.4% disulfide, and 0.4% tetrasulfide.

Another run was carried out the same way as the first run described above except that 10 g of iron powder and 20 g of trisulfide were used. The iron powder failed to remove any significant amount of tetrasulfide.

EXAMPLE III

This example illustrates the preparation of di-t-butyl trisulfide using triethylamine as catalyst.

To a 12 liter 3-neck flask equipped with condenser, thermowell, and magnetic stir bar was added 6000 g (66.5 mol) t-butyl mercaptan and 64 g (0.63 mol) triethylamine. The solution was heated to 50° C. and 1704 g (53.2 mol) sulfur (sublimed or flowers of sulfur) was added in small portions over 5 hours at 50° C. An additional 300 g of t-butyl mercaptan was then added to the reaction mixture, and it was heated to reflux (~80° C.). With time the reflux temperature rose 100° C. The reaction mixture was refluxed for a total of 10 hours. GC analysis of the liquid showed it consisted of 16% t-butyl mercaptan, 67% di-t-butyl trisulfide, 15% di-t-butyl tetrasulfide, 1% di-t-butyl-pentasulfide and 1% other products. Lights were removed by vacuum stripping (10 torr, 100° C., 2 hours). After filtration using Celite 545 and fluted filter paper, 5130 g of a clear yellow liquid was obtained. GC analysis showed the yellow liquid consisted of 80.9% trisulfide, 17.2% tetrasulfide, 0.9% pentasulfide, 0.2% disulfide, and 0.8% other products.

The liquid was distilled using a Vigreux column. Distillation at 2 torr (pot temperature 80°–96° C., head temperature 63°–70° C., reflux ratio 1/1) gave 3180 g of a pale yellow liquid that contained 96.5% trisulfide, 2.8% tetrasulfide and 0.7% disulfide. Alternatively, distillation at 2 torr (pot temperature 80°–113° C., head temperature 63°–96° C.) gave 4258 g of a yellow liquid that contained 91.2% trisulfide, 8.4% tetrasulfide, and 0.4% disulfide.

The product of the reaction was distilled under reduced pressure to give a product containing (by GC) 95.3% di-t-butyl trisulfide, 3.2% disulfide and 1.0% tetrasulfide.

EXAMPLE IV

This example illustrates the removal of tetrasulfide from distilled di-t-butyl trisulfide. To a 250 ml flask with a thermowell, magnetic stir bar, and condenser was added 60.0 g of di-t-butyl trisulfide (prepared in Example III) and 4.0 g of copper powder (Fisher Scientific C431). The mixture was heated to 150° C. with stirring and maintained at 150° C. for 30 minutes. After cooling, the reaction mixture was filtered to give 59.4 g of a clear yellow liquid which contained (by GC) 94.7% di-t-butyl trisulfide, 3.9% disulfide, and 0.2% tetrasulfide. The yield was 99%.

EXAMPLE V

This example demonstrates that organic polysulfide compounds having low content of tetrasulfides or higher polysulfides have much reduced metal corrosiveness. The runs were carried out by the following procedure: A high purity copper coupon or strip (20 mm×49 mm×1 mm containing 7 mm diameter hole) was sanded with 240 grit paper and wiped clean with a paper towel. The copper coupon was then weighed to nearest 0.0001 g. The coupon was then placed in a test tube (25 mm×150 mm) and covered with 25.0 ml of di-t-butyl trisulfide sample. The tube (open) was then placed in a mineral oil bath (magnetically stirred) at 120° C. for 3.0 hours. The liquid level in the tube was 1 inch below level of mineral oil. The tube was removed from bath and the coupon was taken out with forceps and cooled. The coupon was washed with heptane and dried. The coupon was placed, with tongs or forceps, in aqueous sodium cyanide solution (15 g sodium cyanide in 150 mls distilled water) for 1–2 minutes to remove all black corrosion (gloves should be worn and procedure should be carried out in hood). The coupon was then removed and washed in running water in a sink in the hood. The strip was dried with acetone and then heptane and wiped dry with a paper towel. The weight loss was determined by weighing the coupon to nearest 0.0001 g. The results are shown in Table I below.

TABLE I

| Copper Corrosion Tests of Di-t-Butyl Trisulfide Samples[a] | |
| --- | --- |
| Polysulfide | Weight Loss (g) of Copper Coupon[b] |
| Sample prepared in Example III without distillation | 0.4252 |
| Distilled sample containing 97.8% trisulfide and 1.0% tetrasulfide | 0.0066 |
| Same distilled sample (above) with one gram sulfur added | 0.4957 |
| Distilled sample containing 96.5% trisulfide and 2.8% tetrasulfide | 0.0250 |
| Distilled sample containing 91.2% trisulfide and 8.4% tetrasulfide | 0.0556 |
| Distilled sample containing 78.0% trisulfide and 21.0% tetrasulfide | 0.1079 |
| Distilled sample containing 40.0% trisulfide and 59.4% tetrasulfide | 0.2080 |
| Distilled sample containing 7.6% trisulfide, 85.0% tetrasulfide, and 6.7% pentasulfide | 0.3298 |

[a]See Example III.
[b]All copper coupons had same surface area.

Table I shows that metal corrosion increased with increasing concentration of di-t-butyl tetrasulfide or sulfur in the di-t-butyl trisulfide preparation.

EXAMPLE VI

This example illustrates the preparation of an organic disulfide which is contaminated with an organic trisulfide.

To a 250 ml, 3-necked flask equipped with a thermowell, magnetic stir bar, and condenser was added 0.30 g of 50% aqueous NaOH, 1.93 g of Tergitol® 15-S-7 (Union Carbide), and 60.0 g of n-octyl mercaptan. The mixture was heated to 50° C. with stirring. The 3.4 g of sulfur powder was added in portions over 4–5 minutes. Hydrogen sulfide was given off. Immediately after the sulfur was added, a 0.5 ml sample was taken for GC analysis. After 15 minutes of reaction, the polysulfide product containing di-n-octyl disulfide, di-n-octyl trisulfide was recovered.

EXAMPLE VII

This example illustrates the removal of trisulfide from di-n-octyl disulfide. A di-n-octyl disulfide sample obtained in Example VI which contained 98.6% disulfide and 1.2% trisulfide was treated with copper powder by the following procedure.

To a 250 ml flask with a thermowell, magnetic stir bar, and condenser was added 60.0 g of the di-n-octyl disulfide sample described above and 6.0 g of copper powder (Fisher Scientific C431). The mixture was heated to 150° C. with stirring and maintained at 150° C. for 1 hour. After cooling, the reaction mixture was filtered to give 58.4 g of a yellow liquid which contained (by GC) 99.7% di-n-octyl disulfide and less than 0.1% trisulfide. The yield was 97%.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the specification and the claims.

That which is claimed:

1. A process for producing a polysulfide having reduced metal corrosiveness comprising contacting an organic polysulfide having the formula of $RS_nR$ with a transition metal selected from the group consisting of copper, zinc, nickel, and combinations of two or more thereof wherein said polysulfide is prepared by the reaction of a mercaptan and elemental sulfur catalyzed by a basic catalyst; each R is independently selected from a hydrocarbyl radical having 1 to about 30 carbon atoms; n is a number from 2 to about 10; and said hydrocarbyl radical is selected from the group consisting of alkyl, cycloalkyl, and combinations of two or more thereof.

2. A process according to claim 1 wherein said hydrocarbyl radical contains 2 to 15 carbon atoms.

3. A process according to claim 1 wherein said hydrocarbyl radical is an alkyl radical.

4. A process according to claim 1 wherein n is a number from 2 to 5.

5. A process according to claim 1 wherein said polysulfide is selected from the group consisting of di-t-butyl trisulfide, di-t-butyl disulfide, and combinations thereof.

6. A process according to claim 1 wherein said polysulfide is di-n-octyl disulfide.

7. A process according to claim 1 wherein said transition metal is copper.

8. A process according to claim 1 wherein said contacting is carried out at a temperature in the range of from about 20° C. to about 300° C.

9. A process according to claim 1 wherein said contacting is carried out at a temperature in the range of from 80° C. to 200° C.

10. A process according to claim 1 wherein the weight ratio of said transition metal to said polysulfide is in the range of from about 0.001:1 to about 10:1.

11. A process according to claim 1 wherein the weight ratio of said transition metal to said polysulfide is in the range of from 0.001:1 to 0.5:1.

12. A process for reducing the metal corrosiveness of a polysulfide compound comprising contacting said polysulfide with a transition metal selected from the group consisting of copper, zinc, nickel and combinations of two or more thereof wherein said polysulfide is prepared by the reaction of a mercaptan and elemental sulfur catalyzed by a basic catalyst and has a general formula of $RS_nR$; each R is independently selected from a hydrocarbyl radical having 1 to about 30 carbon atoms, n is a number from 2 to about 10; said transition metal is present in an amount sufficient to effect the preparation of a treated polysulfide having reduced metal corrosiveness as compared to said polysulfide; and said hydrocarbyl radical is selected from the group consisting of alkyl, cycloalkyl, and combinations of two or more thereof.

13. A process according to claim 12 wherein said hydrocarbyl radical is an alkyl radical.

14. A process according to claim 12 wherein n is a number from 2 to 5.

15. A process according to claim 12 wherein said polysulfide is selected from the group consisting of di-t-butyl trisulfide, di-t-butyl disulfide, and combinations thereof.

16. A process according to claim 12 wherein said polysulfide is di-n-octyl disulfide.

17. A process according to claim 12 wherein said transition metal is copper.

18. A process according to claim 12 wherein said contacting is carried out at a temperature in the range of from 80° C. to 200° C.

19. A process according to claim 12 wherein the weight ratio of said transition metal to said polysulfide is in the range of from 0.001:1 to 0.5:1.

20. A process for reducing the concentration of a polysulfide having 4 or more sulfur atoms in the molecule in a polysulfide mixture comprising contacting said polysulfide mixture with a transition metal selected from the group consisting of copper, zinc, nickel and combinations of two or more thereof wherein said polysulfide mixture has a general formula of $RS_nR$, each R is independently selected from a hydrocarbyl radical having 1 to about 30 carbon atoms; n is a number from 2 to about 10; and said transition metal is present in an amount sufficient effective to substantially reducing the content of said polysulfide having 4 or more sulfur atoms.

21. A process according to claim 20 wherein said hydrocarbyl radical is an alkyl radical.

22. A process according to claim 20 wherein n is a number from 2 to 5.

23. A process according to claim 20 wherein said transition metal is a transition metal.

24. A process according to claim 20 wherein said transition metal is copper.

25. A process according to claim 20 wherein said contacting is carried out at a temperature in the range of from 80° C. to 200° C.

26. A process according to claim 20 wherein the weight ratio of said transition metal to said polysulfide is in the range of from 0.001:1 to 0.5:1.

27. A process for reducing the concentration of an organic trisulfide from a mixture containing an organic disulfide and said trisulfide comprising contacting said mixture with a transition metal selected from the group consisting of copper, zinc, nickel, and combinations of two or more thereof wherein said mixture is prepared by the reaction of a meracaptan and elemental sulfur catalyzed by a basic catalyst and has the formula of $RS_nR$; each R is independently selected from a hydrocarbyl radical having 1 to about 30 carbon atoms, n is 2 or 3; said transition metal is present in an mount sufficient to effect the reduction of the content of said trisulfide; and said hydrocarbyl radical is selected from the group consisting of alkyl, cycloalkyl, and combinations of two or more thereof.

28. A process according to claim 27 wherein said hydrocarbyl radical is an alkyl radical.

29. A process according to claim 27 wherein said transition metal is copper.

30. A process according to claim 27 wherein said contacting is carried out at a temperature in the range of from 80° C. to 200° C.

31. A process according to claim 27 wherein the weight ratio of said transition metal to said polysulfide is in the range of from 0.001:1 to 0.5:1.

* * * * *